(12) United States Patent
Choi (10) Patent No.: US 9,303,243 B2
(45) Date of Patent: Apr. 5, 2016

(54) DRY ANAEROBIC COMPOSTING FACILITY

(71) Applicant: Hong Lim Choi, Seoul (KR)

(72) Inventor: Hong Lim Choi, Seoul (KR)

(73) Assignee: Resourcification Research Center for Crop-Animal Farming, Seoul (KR)

( * ) Notice: Subject to any disclaimer, the term of this patent is extended or adjusted under 35 U.S.C. 154(b) by 127 days.

(21) Appl. No.: 14/257,667

(22) Filed: Apr. 21, 2014

(65) Prior Publication Data
US 2015/0299632 A1   Oct. 22, 2015

(51) Int. Cl.
| | |
|---|---|
| *C12M 3/00* | (2006.01) |
| *C05F 11/00* | (2006.01) |
| *C12M 1/34* | (2006.01) |
| *C12M 1/107* | (2006.01) |
| *C12M 1/00* | (2006.01) |
| *C12M 1/06* | (2006.01) |

(52) U.S. Cl.
CPC ............... *C12M 41/12* (2013.01); *C12M 21/04* (2013.01); *C12M 23/18* (2013.01); *C12M 23/34* (2013.01); *C12M 23/36* (2013.01); *C12M 23/38* (2013.01); *C12M 27/02* (2013.01); *C12M 41/40* (2013.01); *C12M 45/06* (2013.01); *C12M 47/18* (2013.01); *Y02E 50/343* (2013.01)

(58) Field of Classification Search
CPC .......... C02F 11/00; C02F 3/00; C12M 21/04; C12M 21/16
See application file for complete search history.

(56) References Cited

U.S. PATENT DOCUMENTS

| | | | | |
|---|---|---|---|---|
| 5,102,803 | A * | 4/1992 | Weaver ............... | C05F 17/0072 261/87 |
| 5,269,634 | A * | 12/1993 | Chynoweth ............... | B09B 1/00 405/129.25 |
| 5,496,730 | A * | 3/1996 | Teramachi .......... | C05F 17/0027 435/290.2 |
| 6,399,366 | B1 * | 6/2002 | Seagren ............... | C05F 17/0211 241/101.2 |
| 2006/0057711 | A1 * | 3/2006 | Timm .................. | C05F 17/0258 435/290.1 |
| 2011/0045580 | A1 * | 2/2011 | Hater ........................ | B09B 1/00 435/290.4 |
| 2014/0157777 | A1 * | 6/2014 | Kramer ..................... | C12P 3/00 60/641.8 |

* cited by examiner

*Primary Examiner* — Nathan Bowers
(74) *Attorney, Agent, or Firm* — Rabin & Berdo, P.C.

(57) ABSTRACT

Disclosed is a dry anaerobic composting facility. More specifically, disclosed is a dry anaerobic composting facility which mixes organic waste with a water controller by a pretreatment unit, followed by pressing, grinding and substitution to convert the organic waste into an anaerobic substance, continuously subjects the anaerobic compound to fermentation, mixing/grinding, transport and discharge using an agitator by an anaerobic fermentation unit to improve production of compost, ages the produced compost by a post-aging unit to provide high-quality compost, and collects biogas produced by the anaerobic fermentation unit and uses the biogas as an energy source of a self-generator or a combined heat and power generator, to realize energy self-generation.

13 Claims, 11 Drawing Sheets

DRY ANAEROBIC COMPOSTING FACILITY

BACKGROUND OF THE INVENTION

1. Field of the Invention

The present invention relates to a dry anaerobic composting facility. More specifically, the present invention relates to a dry anaerobic composting facility which mixes organic waste with a water controller in a pre-treatment unit, followed by pressing, grinding and substitution to convert the organic waste into an anaerobic substance, continuously subjects the anaerobic compound to fermentation, mixing/grinding, transport and discharge using an agitator in an anaerobic fermentation unit to improve production of compost, ages the produced compost in a post-aging unit to provide high-quality compost, and collects biogas produced by the anaerobic fermentation unit and uses the biogas as an energy source of a self-generator or a combined heat and power generator to realize energy self-generation.

2. Description of the Related Art

In recent years, biogas such as methane produced through anaerobic digestion of organic waste such as food waste, livestock excretions and sewage sludge is used for combined heat and power generation and the like.

Such production of biogas from organic waste and use thereof attract much attention in that biogas is used as an energy source and reduction in environmental pollution such as non-discharge of pollutants to water and air and reduction of greenhouse gas emission is possible.

A common anaerobic treatment method which is the most generally used all over the world uses no composting facility, thus causing complaints from nearby residents due to unpleasant odor generated during decomposition of organic substances.

However, this anaerobic treatment method disadvantageously has a difficulty in securing land, in particular, in Korea, due to being mounted on the ground, and has low economic efficiency because heat loss caused by conduction and convection by low temperature and wind in winter may require supply of more auxiliary heat.

In addition, the conventional anaerobic treatment method includes supply of air to facilitate biodegradation of organic substances, thus causing deterioration in nitrogen component due to nitrification and having a problem associated with compost qualities.

SUMMARY OF THE INVENTION

Therefore, the present invention has been made in view of the above problems, and it is one object of the present invention to provide a dry anaerobic composting facility which converts organic waste into an anaerobic low-molecular weight compound through hydrolysis and acid fermentation by a pre-treatment unit connected to a dry anaerobic fermentation unit and then supplies the organic waste to the dry anaerobic fermentation unit, before fermenting the organic waste by the dry anaerobic fermentation unit laid under the ground, mixes the organic waste with water controllers (sawdust and chaff) using an agitator in the dry anaerobic fermentation unit and facilitates methane fermentation through suction, grinding, transport and discharge operations to improve production of compost, ages the produced compost by a post-aging unit to provide high-quality compost, and collects biogas produced by the dry anaerobic fermentation unit to remove generated odor and uses the biogas as an energy source of a self-generator or a combined heat and power generator to realize energy self-generation.

It is another object of the present invention to provide a dry anaerobic composting facility which minimizes energy loss using geothermal heat and efficiently uses a ground space because it is laid under the ground, and solves problems including environmental pollution as well as complaints from inhabitants due to unpleasant facilities because it is mounted adjacent to residential areas.

In accordance with an aspect of the present invention, the above and other objects can be accomplished by the provision of a dry anaerobic composting facility including a dry anaerobic fermentation unit for composting organic waste as a low-molecular weight compound pre-treated in absence of oxygen through covers doubly overlaid on an open top of an anaerobic fermentation tank laid under the ground, by methane fermentation while agitating the organic waste by an agitator, and collecting biogas generated during the methane fermentation by a collector provided in an attic space of a ceiling, a pre-treatment unit laid under the ground such that the pre-treatment unit is connected to the anaerobic fermentation tank, the pre-treatment unit converting the organic waste, which is supplied to a primary fermentation tank through the gate and is retained therein for several hours to several days, into low-molecular weight compounds through hydrolysis and acid fermentation and then converting the low-molecular weight compounds and the biogas, which are supplied to a substitution tank, from an aerobic state to an anaerobic state by substitution reaction and supplying the anaerobic substances to the dry anaerobic fermentation unit, and a post-treatment unit for aging a portion of fermented compost supplied to a post-aging tank laid under the ground while being connected to the anaerobic fermentation tank, or discharging the compost, wherein the pre-treatment unit is isolated from the dry anaerobic fermentation unit through a first barrier which automatically rises and lowers, the post-treatment unit is isolated from the dry anaerobic fermentation unit through a fixed barrier provided with a transport screw, and the pre-treatment unit and the post-treatment unit include a gate provided in a portion of an upper part of the primary fermentation tank and a gate provided in a portion of an upper part of the post-aging tank, respectively, to receive the organic waste or discharge the produced compost.

The covers may be doubly overlaid based on a duct frame connected to an exterior vacuum pump to maintain an inside of the cover under vacuum and is provided on the surface thereof with a plurality of solar modules for producing electricity from sunlight and providing the electricity as an energy source of a combined heat and power generator.

The biogas collected by the collector may be used as an energy source of the combined heat and power generator and the electricity produced by the combined heat and power generator is used as a power source of a heater and a lighting provided in the anaerobic fermentation tank, the primary fermentation tank, the substitution tank and the post-aging tank, and as a power source of the agitator, the first barrier and the transport screw, to realize energy self-generation.

The heater may be a heat pipe or a warm water pipe.

The pre-treatment unit may have a bottom surface inclined in one direction so that the organic waste is supplied to the anaerobic fermentation tank by self-weight.

A first rail may be mounted at both sides in a longitudinal direction of the anaerobic fermentation tank, a second rail moved along the first rail may be mounted in an upper part of the first rail, and the agitator may be mounted on the second rail.

The agitator may include a suction unit for suctioning the organic waste in the anaerobic fermentation tank, and grinding and agitating the organic waste, a transport unit for transporting the organic waste ground by the suction unit, a discharge unit connected to the transport unit, for discharging the organic waste, a movement unit for moving the suction unit in a vertical direction and moving the discharge unit in a longitudinal direction and a width direction of the anaerobic fermentation tank, and a control unit for controlling the suction unit, the transport unit, the discharge unit and the movement unit.

The control unit may further include a sensor for acquiring data including viscosity of organic waste, temperature, pressure, ground particle size, water and gas discharge level and determining a state of the organic waste, and performs a general function of controlling the suction unit, the transport unit, the discharge unit and the movement unit according to data acquired by the sensor.

The movement unit may include a first motor for moving the agitator in a longitudinal direction of the anaerobic fermentation tank, a second motor for moving the agitator in a width direction of the anaerobic fermentation tank, and a hydraulic cylinder for moving the suction unit of the agitator in a vertical direction.

The suction unit may include a suction screw body rotating under control of the control unit, suction screw blades mounted on the suction screw body, the suction screw blades moving the organic waste toward the center of the suction screw body upon rotation, and a suction screw cover disposed on a rear surface of the suction screw body into which the organic waste is injected, the suction screw cover press-grinding the organic waste together with the suction screw blades.

The discharge unit may include a discharge screw body rotating under control of the control unit, a discharge screw blade mounted on the discharge screw body, the discharge screw blade distributing the organic waste ground by the suction unit and transported along the transport unit, in a longitudinal direction of the discharge screw body upon rotation, and a discharge screw cover disposed on the rear surface of the discharge screw blade.

The primary fermentation tank and the substitution tank of the pre-treatment unit may be isolated from each other via a second barrier which automatically rises and lowers.

A downspout plate for collecting rain may be mounted on an end of the cover and a rain collection tank connected to the downspout plate for storing rain collected in the downspout plate is laid in the ground.

The duct frame may be made of a flexible material so that the cover sags due to weight of a plurality of solar modules mounted on the surface of the cover and my swell due to the biogas produced in the anaerobic fermentation tank.

The anaerobic fermentation tank may have a bottom inclined with respect to one side, a leachate collection unit for collecting a leachate of the organic waste may be provided in a lower part of the one side, and a filter for allowing for injection of only leachate into the leachate collection unit may be provided on the top of the leachate collection unit.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
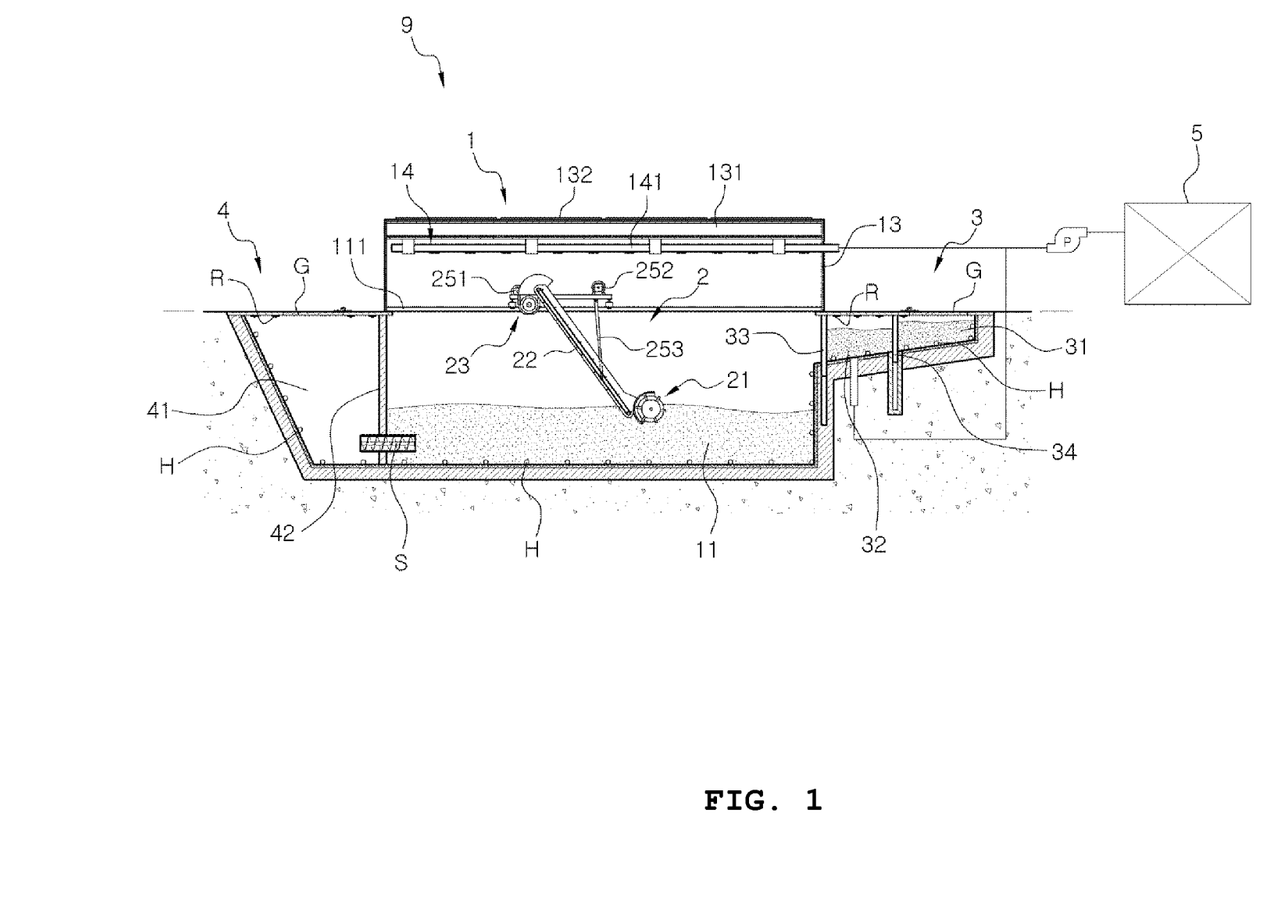
FIG. 1 is a sectional view illustrating a configuration of a dry anaerobic composting facility according to the present invention.
Figure 2:
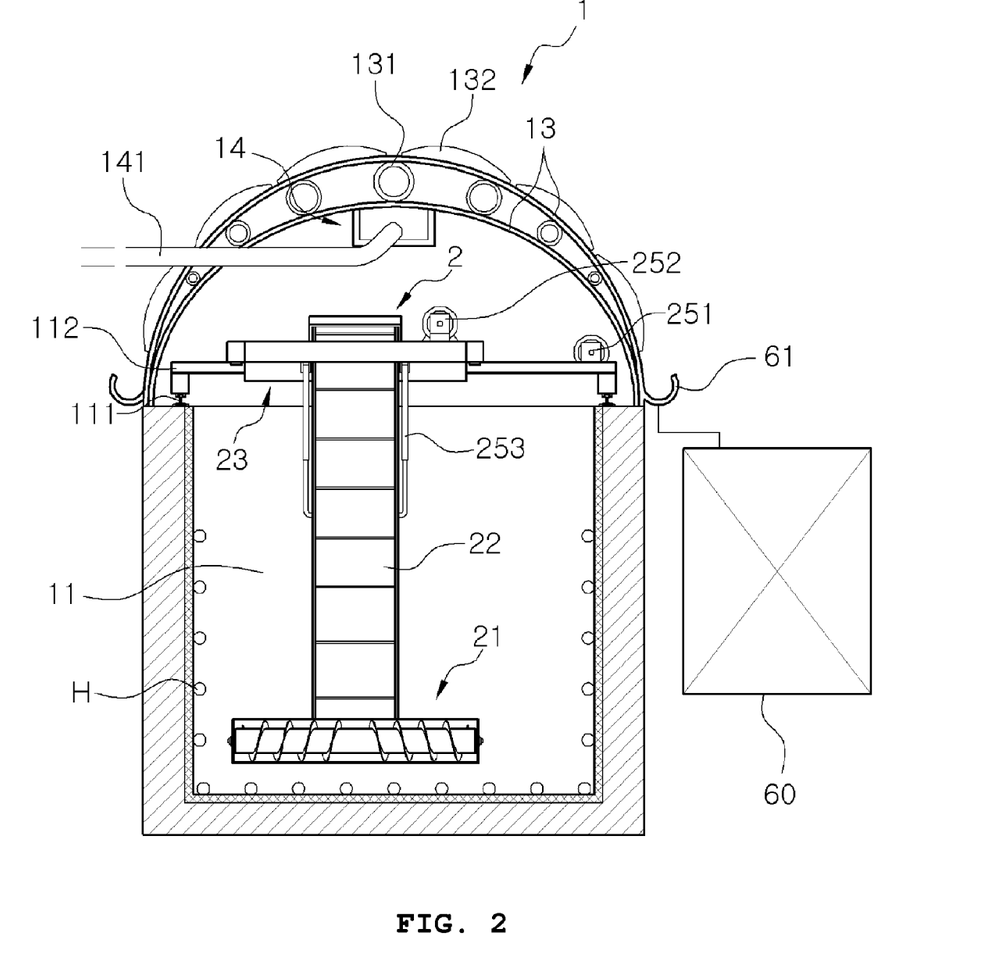
FIG. 2 is a front sectional view illustrating a configuration of a dry anaerobic fermentation unit of FIG. 1.
Figure 3:
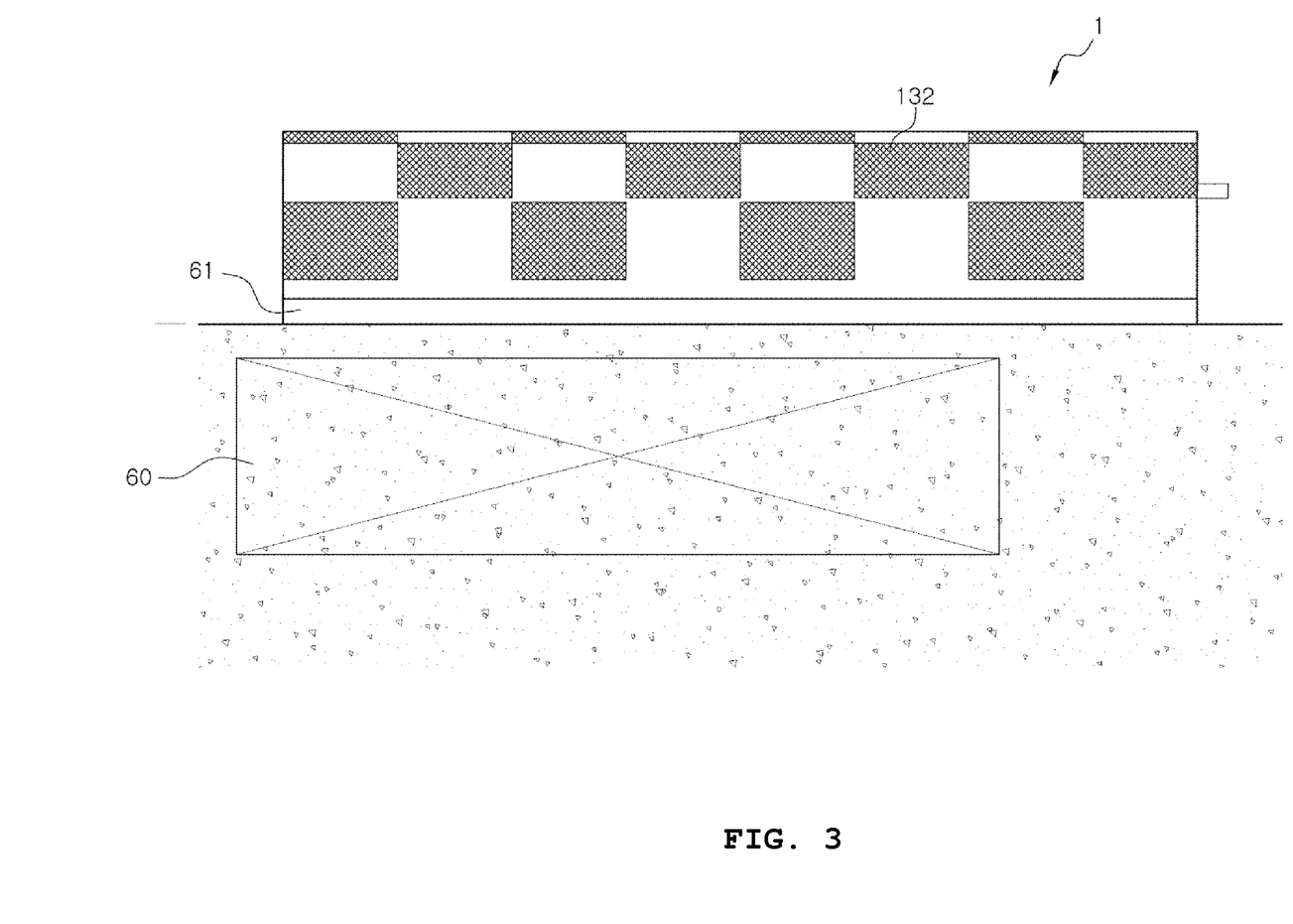
FIG. 3 is a side view of the dry anaerobic fermentation unit of FIG. 2.
Figure 4:
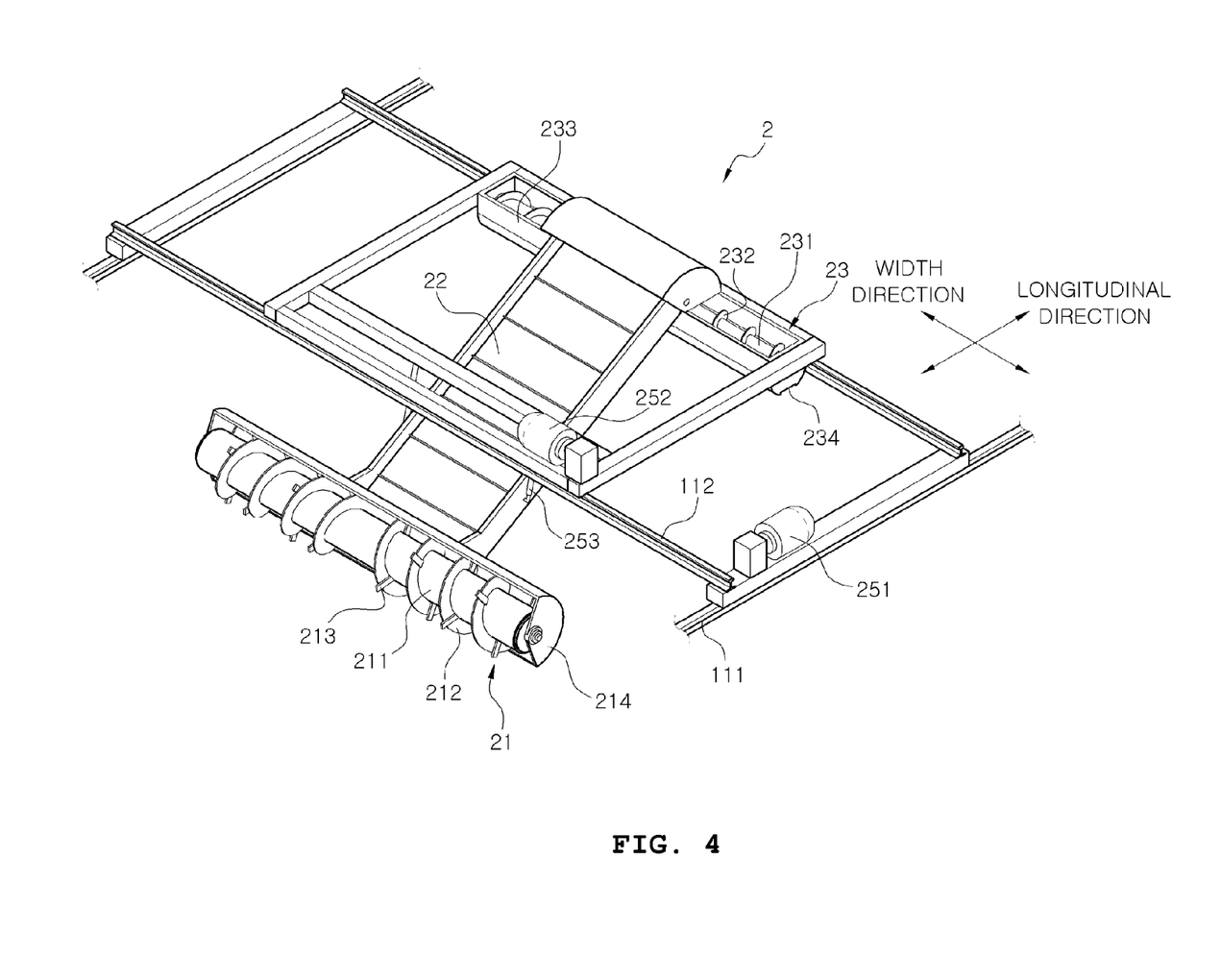
FIG. 4 is a perspective view illustrating an agitator shown in FIG. 1.
Figure 5:
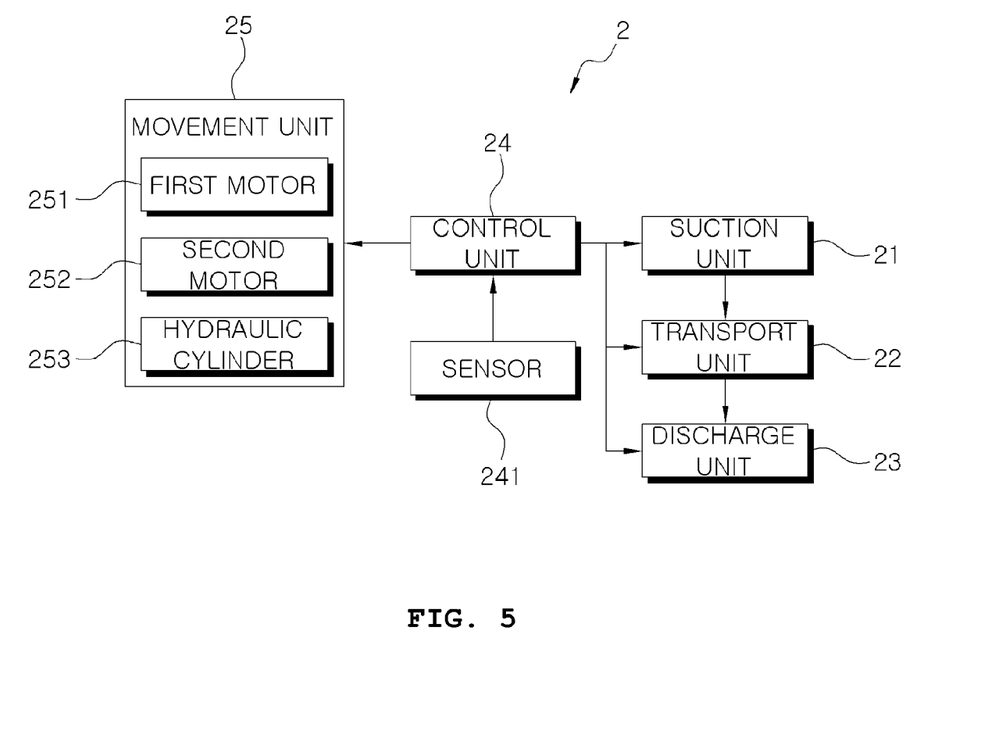
FIG. 5 is a block diagram illustrating the agitator.

Hereinafter, a dry anaerobic composting facility according to the present invention will be described in detail with reference to the annexed drawings:

FIG. 1 is a sectional view illustrating a configuration of a dry anaerobic composting facility according to the present invention, FIG. 2 is a front sectional view illustrating a configuration of a dry anaerobic fermentation unit of FIG. 1, FIG. 3 is a side view of the dry anaerobic fermentation unit of FIG. 2, FIG. 4 is a perspective view illustrating an agitator shown in FIG. 1, and FIG. 5 is a block diagram illustrating the agitator. As shown in FIGS. 1 to 5, the present invention provides a dry anaerobic composting facility 9 which converts organic waste into anaerobic low-molecular weight compounds through hydrolysis and acid fermentation in a pre-treatment unit connected to a dry anaerobic fermentation unit and then supplies the organic waste to the dry anaerobic fermentation unit before fermenting the organic waste by the dry anaerobic fermentation unit laid under the ground, mixes the organic waste with water controllers (sawdust and chaff) using an agitator 2 in the dry anaerobic fermentation unit and facilitates methane fermentation through suction, grinding, transport and discharge operations to improve production of compost, ages the produced compost in a post-aging unit to provide high-quality compost, and collects biogas produced by the dry anaerobic fermentation unit and uses the biogas as an energy source of a self generator or a combined heat and power generator to realize energy self-generation.

The dry anaerobic composting facility 9 of the present invention is broadly composed of three elements, namely, a dry anaerobic fermentation unit 1, a pre-treatment unit 3 and a post-treatment unit 4.

The dry anaerobic fermentation unit 1 includes covers 13 doubly overlaid on an open top of an anaerobic fermentation tank 11 laid under the ground, and functions to compost organic waste as a low-molecular weight compound pre-treated in absence of oxygen by methane fermentation while agitating the organic waste by an agitator 2, and collects biogas generated by methane fermentation by a collector 14 provided on an attic space of the ceiling.

The anaerobic fermentation tank 11 of the dry anaerobic fermentation unit 1 is composed of concrete and is laid under the ground so that temperature variation is minimized and heat insulation is maximized.

In addition, the cover 13 is supported by a duct frame 131 disposed on the open top of the anaerobic fermentation tank 11 and functions to stabilize a compost pile through anaerobes in absence of oxygen, to collect biogas generated during methane fermentation by the collector 14 provided on the ceiling and to then discharge the biogas to the outside.

The cover 13 is made of a transparent vinyl substance so that sunlight is incident thereupon, as shown in FIGS. 2 and 3, and the cover made of vinyl is doubly overlaid based on the duct frame 131 so that an inside of the cover is kept under vacuum. The duct frame 131 is connected to an exterior vacuum pump (not shown) so that an air layer between the overlaid vinyl substances is removed and effect of heat insulation is maximized under vacuum.

In addition, the cover 13 is made of a material upon which sunlight is incident, such as high-density polyethylene (HDPE), PE, LDPE, or polycarbonate, to obtain natural greenhouse effect, maintain the normal inner temperature of the anaerobic fermentation tank 11, prevent temperature drop in winter and thereby facilitate anaerobic fermentation of compost.

In addition, the cover 13 is provided on the surface thereof with a plurality of solar modules 132 which produce electricity from sunlight and supplies the electricity to a combined heat and power generator or supplies the same as a power source of a heater H, a lighting R, a transport screw (S) and an agitator 2 provided in the anaerobic fermentation tank 11, the primary fermentation tank 31 and the post-aging tank 41.

The respective solar modules 132 are alternately disposed such that a surface of the cover 13 is exposed in four directions of the adjacent solar modules 132 and sunlight is thus incident thereupon. This configuration enables power production and introduction of sunlight into the anaerobic fermentation tank 11 through the solar module 132.

In addition, the duct frame 131 is made of a flexible material so that the cover 13 sags under the weight of the solar modules 132 mounted on the surface of the cover 13 and swells due to the biogas produced in the anaerobic fermentation tank 11.

Through this configuration, amount of produced biogas can be determined according to swelling level of the cover 13 and biogas can be forcibly collected by the collection pipe 141 of the collector 14 without power. The collection pipe 141 may be provided inside thereof with a pump p to prevent of explosion of the inside of the cover 13.

In addition, the cover 13 is provided at both ends thereof with a downspout plate 61 for collecting rain and a rain collection tank 60 connected to the downspout plate 61 is laid under the ground so that rain collected in the downspout plate 61 is stored.

The rain collected by the rain collection tank 60 may be used as cleaning water and control water of the dry anaerobic fermentation unit 1, the pre-treatment unit 3 and the post-treatment unit 4 and be used to supply water to other crops, so that use of additional water supply facilities is prevented and facility operating costs are reduced.

In addition, the collector 14 is configured such that the biogas collected through the collection pipe 141 mounted on the attic space of the ceiling is used as an energy source of the combined heat and power generator 5.

The electricity produced by the combined heat and power generator 5 is used as a power source of a heater H provided in the anaerobic fermentation tank 11, a primary fermentation tank 31 and a post-aging tank 41, as a power source of a lighting R, and as a power source of a transport screw (S) and the agitator 2 to realize energy self-generation.

The heater (H) is either a heat pipe or a warm water pipe. In the present invention, the heater (H) is a heat pipe.

Figure 6:
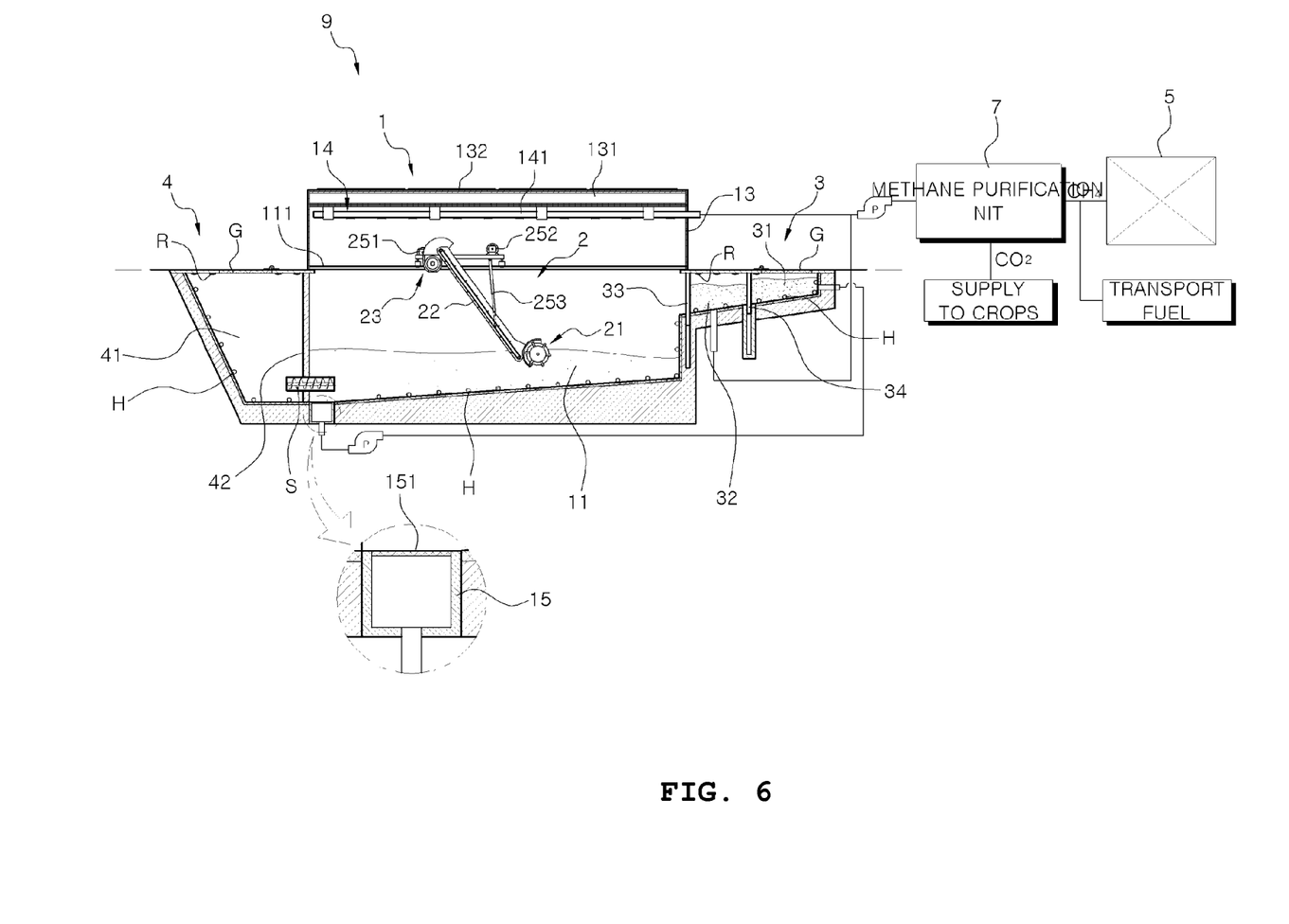
FIG. 6 is a sectional view illustrating a variation example of a configuration of a dry anaerobic composting facility according to the present invention.

In addition, a methane purification unit for separating the biogas into methane and carbon dioxide may be further provided in a line wherein the biogas collected by the collection pipe is supplied to the combined heat and power generator 5, as shown in FIG. 6. The methane purification unit 7 increases a purity of methane that may be used as an energy source or a transport fuel of the combined heat and power generator to 95% or more and separates carbon dioxide. The separated carbon dioxide may be injected into a house (not shown) though an additional line to boost photosynthesis of crops.

The agitator 2 mounted in the anaerobic fermentation tank 11 of the dry anaerobic fermentation unit 1 includes a suction unit 21, a transport unit 22, a discharge unit 23, a movement unit 25 and a control unit 24.

The suction unit 21 functions to suction organic waste in the anaerobic fermentation tank 11, and to grind and agitate the same.

The suction unit 21 includes a suction screw body 211, which rotates under control of the control unit 24, suction screw blades 212, which are mounted on the suction screw body 211 and move the organic waste toward the center of the suction screw body 211 upon rotation, and a suction screw cover 214 which is disposed on a rear surface of the suction screw body 211 into which the organic waste is injected, and presses and grinds the organic waste together with the suction screw blade 212.

The suction screw blades 212 are disposed at both sides of the suction screw body 211 such that the suction screw blades 212 are mutually symmetric, and the organic waste is moved to the center of the suction screw body 211, when the respective suction screw blades 212 rotate. The suction screw blade 212 is further provided with a grinding blade 213 to grind the organic waste moved to the center of the suction screw body 211.

The suction screw cover 214 disposed on the rear surface of the suction screw body 211 is mounted using a hydraulic cylinder, gear or other well-known device such that a distance of the suction screw cover 214 from the suction screw body 211 is changeable, to control pressing of organic waste.

Accordingly, the organic waste is pressed and ground by the suction unit 21 and is carried to the transport unit 22 through the suction screw cover 214.

The transport unit 22 may include a conveyer belt and utilize another mechanical configuration such as an elevator.

The discharge unit 23 includes a discharge screw body 231 which rotates under control of the control unit 24, a discharge screw blade 232 which is mounted on the discharge screw body 231, distributes the organic waste, ground by the suction unit 21 and transported along the transport unit 22, in a longitudinal direction of the discharge screw body 231 upon rotation, and a discharge screw cover 233 disposed on the rear surface of the discharge screw blade 232.

The discharge screw blades 232 are disposed at both sides of the discharge screw body 231 such that the discharge screw blades 232 are mutually symmetric so as to move the organic waste to the outside of the discharge screw body 231 when the discharge screw blades 232 rotate.

In addition, the discharge screw cover 233 is provided at the bottom thereof with an outlet 234 such that the organic waste moved by the discharge screw blade 232 is dropped through the outlet 234.

Meanwhile, the control unit 24 further includes a sensor 241 for acquiring data including viscosity of organic waste, temperature, pressure, ground particle size, and water and gas discharge levels and determining the state of the organic waste, and performs a general function of controlling the suction unit 21, the transport unit 22, the discharge unit 23 and the movement unit 25 according to data acquired by the sensor 241.

The movement unit 25 includes a first motor 251 for moving the agitator 2 in a longitudinal direction of the anaerobic fermentation tank 11, a second motor 252 for moving the agitator 2 in a width direction of the anaerobic fermentation tank 11, and a hydraulic cylinder 253 for moving the suction unit 21 of the agitator 2 in a vertical direction.

A first rail 111 is mounted at both sides in the longitudinal direction of the anaerobic fermentation tank 11, a second rail 112 is mounted in an upper part of the first rail 111, and the agitator 2 is mounted on the second rail 112.

The first motor 251 moves the agitator 2 in a longitudinal direction along the first rail 111, the second motor 252 moves the agitator 2 in a width direction along the second rail 112, and the hydraulic cylinder 253 enables the suction unit 21 of the agitator 2 to rotate in a vertical direction.

Accordingly, the agitator 2 moves in front, back, left and right directions from an upper part of the anaerobic fermentation tank 11 through the first motor 251 and the second motor 252, and enables the suction unit of the agitator 2 to move in a vertical direction through the hydraulic cylinder 253, to grind and agitate organic waste stored in the anaerobic fermentation tank.

Furthermore, the dry anaerobic composting facility according to the present invention may be implemented with a partially modified configuration, as shown in FIG. 6. That is, the bottom of the anaerobic fermentation tank 11 is inclined with respect to one side and a leachate collection unit 15 for collecting a leachate of organic waste is provided in a lower part of the one side. A filter 151 for allowing for injection of only leachate into the leachate collection unit is provided on the top of the leachate collection unit 15.

The leachate collected by the leachate collection unit 15 is circulated to the primary fermentation tank 31 through a pipe line and serves as an inoculum. That is, the leachate contains a great amount of microorganisms which ferment organic waste in the anaerobic fermentation tank 11 and aid to fermentation of organic waste injected into the primary fermentation tank 31.

In addition, a pump P may be mounted on the pipe line through which the leachate passes to selectively induce flow of the leachate.

Meanwhile, the pre-treatment unit 3 is laid under the ground such that it is connected to the anaerobic fermentation tank 11 and is separated from the anaerobic fermentation tank 11 through a first barrier 33 which automatically rises and lowers and partitions an inner area.

In addition, the pre-treatment unit 3 is divided into a primary fermentation tank 31 and a substitution tank 32 and is respectively partitioned via a second barrier 34 which automatically rises and lowers.

The pre-treatment unit 3 is provided in a portion of the top thereof with a gate G to receive organic waste from the primary fermentation tank 31 and tightly closes the inside area, and is formed to have a bottom surface inclined in one direction so that the organic waste is supplied by self-weight via the substitution tank 32 to the anaerobic fermentation tank 11.

That is, the pre-treatment unit 3 is isolated from the anaerobic fermentation tank 11 through the first barrier 33 and the pre-treatment unit 3 is also divided into and partitioned into the primary fermentation tank 31 and the substitution tank 32 through the second barrier 34.

The primary fermentation tank 31 receives the organic waste through the gate (G), retains the same for several hours to several days and then converts a high-molecular weight compound into a low-molecular weight compound through hydrolysis and acid fermentation.

In addition, the substitution tank 32 receives the organic waste as the low-molecular weight compound converted by the primary fermentation tank 31 based on the self-weight according to the shape of the inclined bottom surface, and receives a portion of biogas collected by the collector 14 and decreases dissolved oxygen contained in organic waste by substitution reaction to transform an aerobic state into an anaerobic state.

The anaerobic organic waste is supplied to the anaerobic fermentation tank 11 by self-weight when the first barrier 33 is opened.

In addition, the organic waste supplied to the dry anaerobic fermentation unit 1 is mixed with water controllers (sawdust and chaff) and suctioned, ground, transported and discharged through+ the agitator 2 to facilitate anaerobic fermentation and thereby improve production of compost.

Furthermore, the post-treatment unit 4 functions to age a portion of fermented compost supplied to the post-aging tank 41 laid under the ground such that it is connected to the anaerobic fermentation tank 11 or to discharge the same.

The post-aging tank 41 of the post-treatment unit 4 is isolated from the anaerobic fermentation tank 11 of the dry anaerobic fermentation unit 1 via a fixed barrier 42, and the compost of the anaerobic fermentation tank 11 is automatically supplied to the post-aging tank 41 through a transport screw S mounted on the fixed barrier 42 and the post-aging tank 41 ages the compost to produce high-quality compost.

When the gate G formed in the portion of the top of the post-aging tank 41 is opened, the compost aged by the post-aging tank 41 is transported by a conveyer belt or a transport screw and is then used as organic compost for crops or is supplied to an additional compost package line.

Hereinafter, an operation of the dry anaerobic composting facility will be described in brief.

FIGS. 7 to 11 are views illustrating an operation of the dry anaerobic composting facility.

Figure 7:
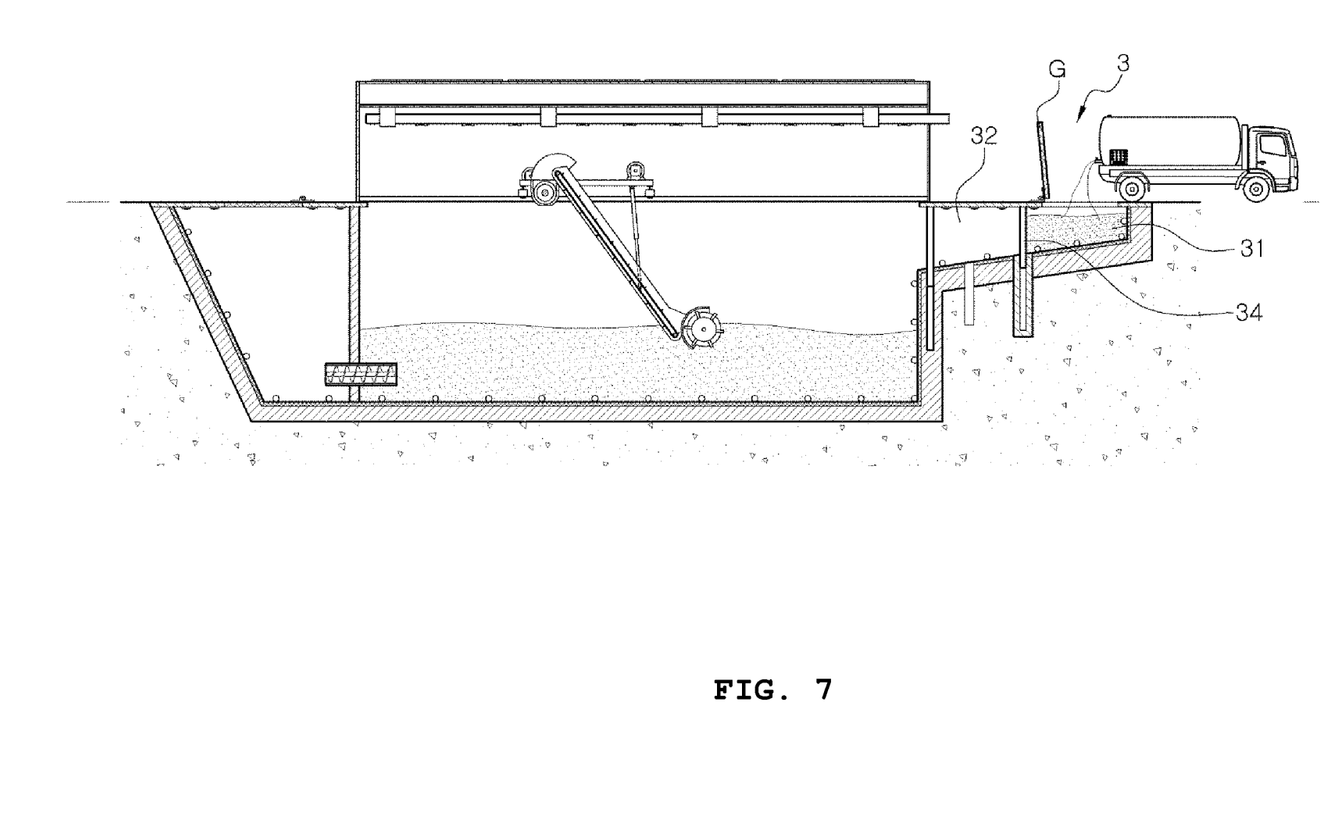
FIGS. 7 to 11 are views illustrating an operation of the dry anaerobic composting facility.

First, as shown in FIG. 7, organic waste (livestock wastewater, livestock excretions, food waste, sewage/waste water sludge) is supplied to the primary fermentation tank 31 when the gate G of the pre-treatment unit 3 is opened. When supply of organic waste is completed, the gate (G) is closed to hermetically seal the primary fermentation tank 31.

The organic waste supplied to the primary fermentation tank 31 is retained for several hours to several days, is hydrolyzed and acid-fermented therein and is then converted into a low-molecular weight compound.

Figure 8:
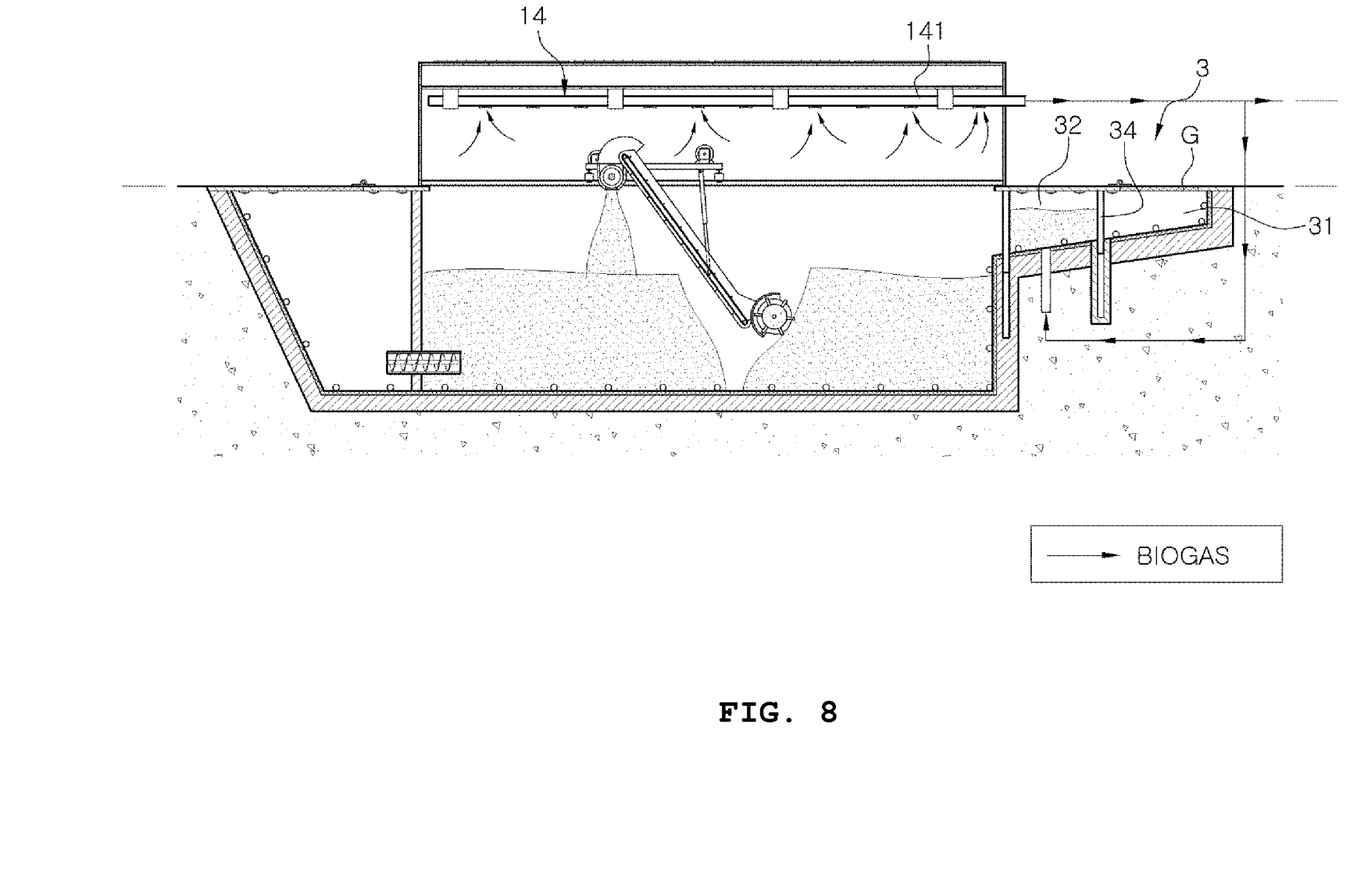

After the primary fermentation, as shown in FIG. 8, when the second barrier 34 is opened, the organic waste present as the low-molecular weight compound in the primary fermentation tank 31 is supplied to the substitution tank 32 by self-weight. Then, the second barrier 34 is elevated and then closed.

The organic waste, as the low-molecular weight compound supplied to the substitution tank 32, receives a portion of biogas collected by the collector 14 to decrease dissolved oxygen contained in the organic waste by substitution reaction and thereby convert the aerobic state into an anaerobic slurry.

Figure 9:
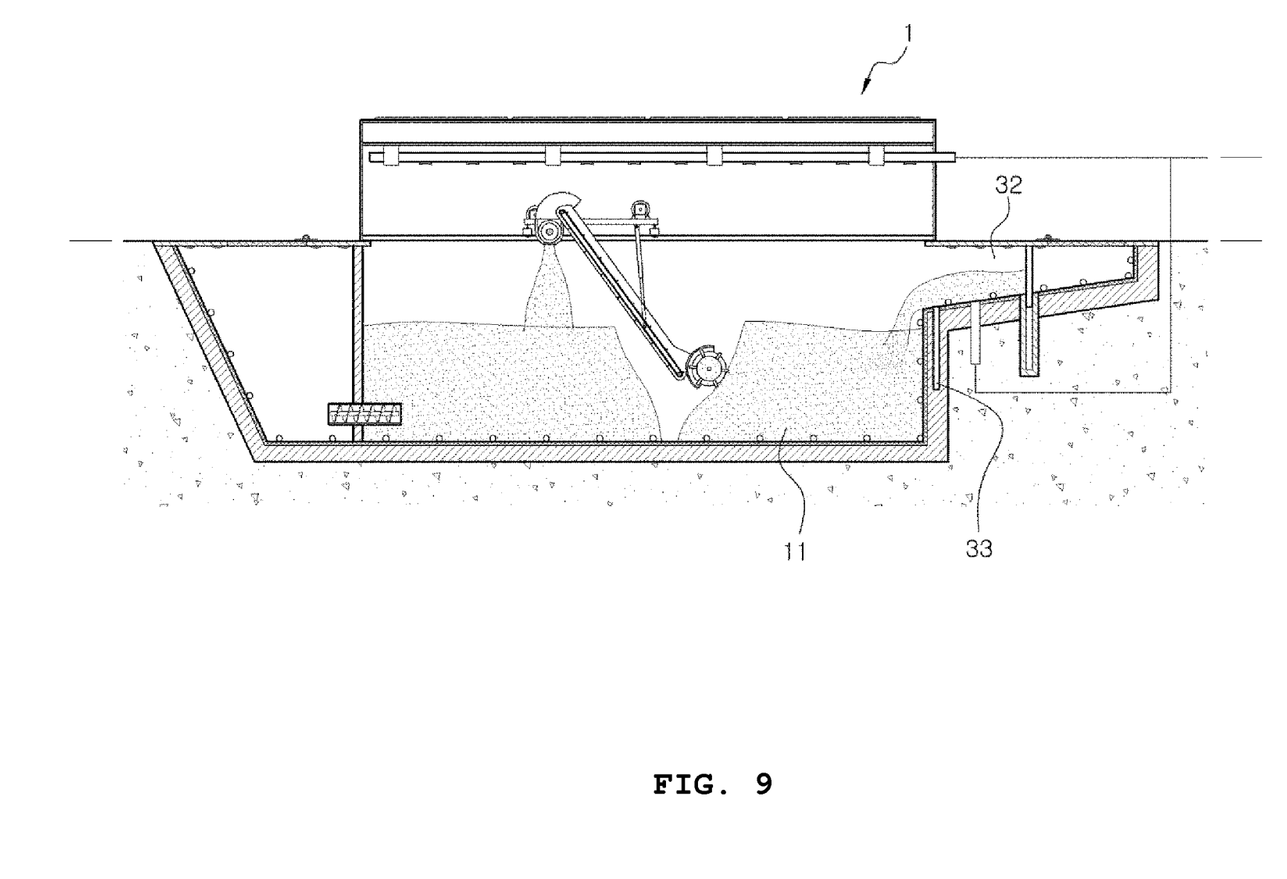

After conversion into the anaerobic state, as shown in FIG. 9, the first barrier 33 is opened and the organic waste is supplied to the anaerobic fermentation tank 11 of the dry anaerobic fermentation unit 1 by the self-weight.

Figure 10:
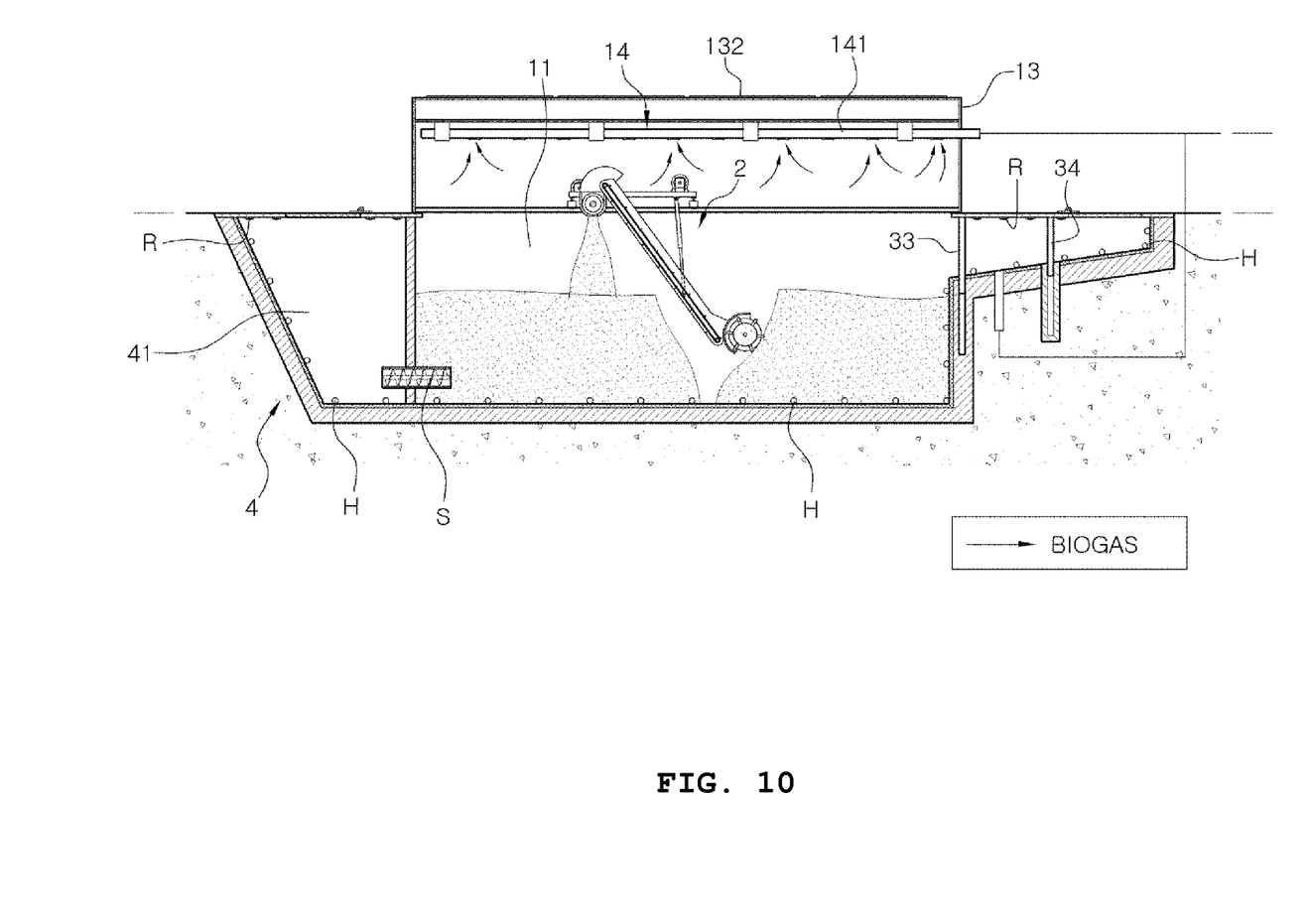

Then, as shown in FIG. 10, when the organic waste supplied to the anaerobic fermentation tank 11 is mixed with water controllers (sawdust and chaff) through the agitator 2, methane fermentation is facilitated by suction, grinding, transport and discharge processes and the organic waste is thus composted within a short time.

The biogas produced during methane fermentation is collected by the collector 14 mounted on the attic space of the ceiling and is then used as an energy source of the combined heat and power generator 5, and electricity generated by the combined heat and power generator 5 is used as a power source of a heater H and lighting R provided in the anaerobic fermentation tank 11, the primary fermentation tank 31, the substitution tank 32, and the post-aging tank 41, and as a power source of the agitator 2, the first barrier 33, the second barrier 34 and the transport screw (S), to realize energy self-generation.

Furthermore, a plurality of solar modules 132 provided on the surface of the cover 13 generate electricity from sunlight, or supply the same to a combined heat and power generator or use the same as a power source of the heater H, the lighting R, the transport screw (S) and an agitator 2 provided in the anaerobic fermentation tank 11, the primary fermentation tank 31 and the post-aging tank 41.

Figure 11:
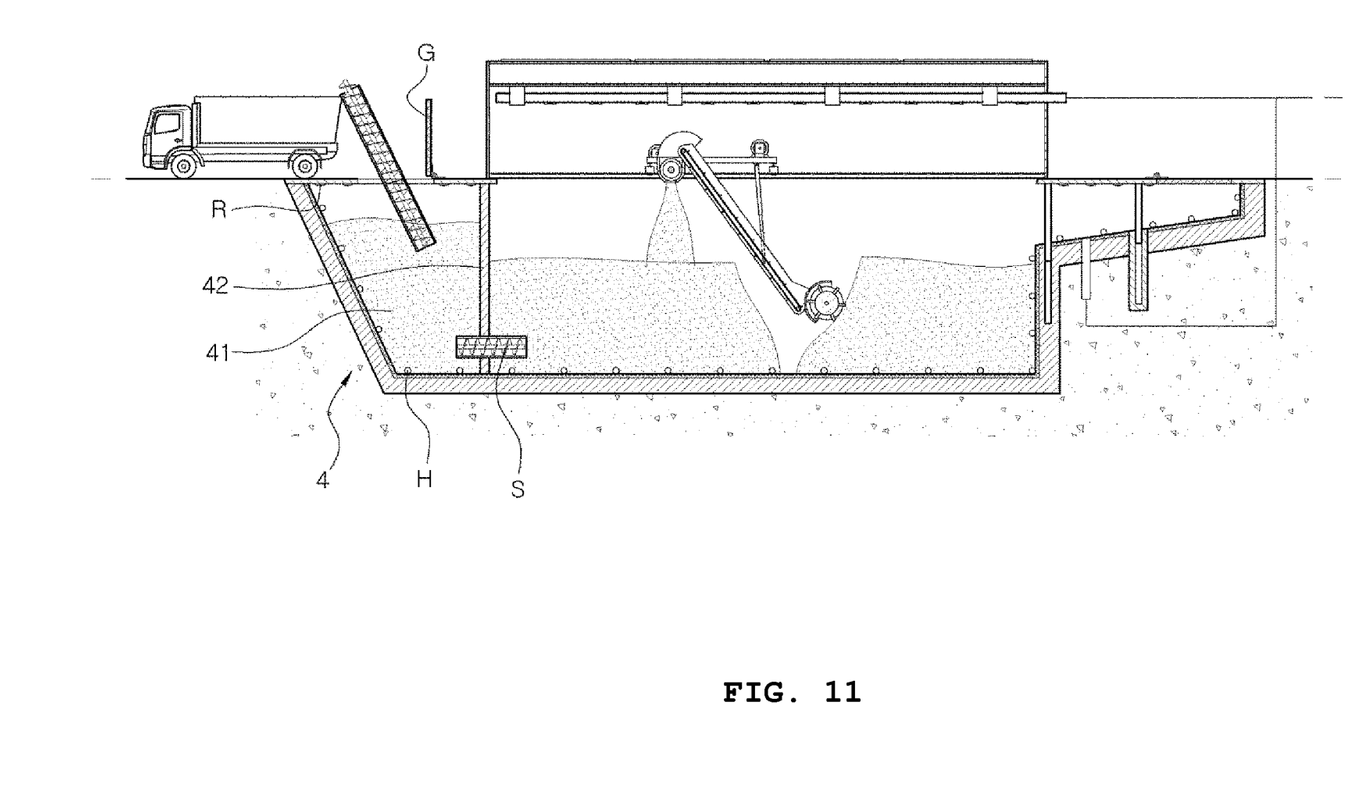

Finally, as shown in FIG. 11, the compost produced by the anaerobic fermentation tank 11 is transported to the post-aging tank 41 of the post-treatment unit 4 through the transport screw (S) mounted on the fixed barrier 42 and is then aged therein to produce high-quality compost, the produced compost is discharged to the outside by the conveyer belt or the transport screw, which is then used as compost of crops or is supplied to an additional compost package line.

Accordingly, according to the present invention, it is possible to eliminate bad odors of organic waste, compost organic waste by fermentation using methane fermentation, and realize energy self-generation through use of biogas produced during methane fermentation as an energy source of a combined heat and power generator. In addition, it is possible to remarkably reduce maintenance and management costs through full-automation of discharge of compost produced by pre-treatment, anaerobic fermentation and post-treatment of organic waste.

As apparent from the above description, the present invention provides a dry anaerobic composting facility which converts organic waste into anaerobic low-molecular weight compounds through hydrolysis and acid fermentation by a pre-treatment unit connected to a dry anaerobic fermentation unit and then supplies the organic waste to the dry anaerobic fermentation unit before fermenting the organic waste by the dry anaerobic fermentation unit laid under the ground, mixes the organic waste with water controllers (sawdust and chaff) using an agitator in the dry anaerobic fermentation unit and facilitates methane fermentation through suction, grinding, transport and discharge operations, thereby advantageously improving production of compost.

The dry anaerobic composting facility ages the produced compost by post-aging unit, thereby discharging high-quality compost. In addition, the dry anaerobic composting facility collects biogas produced by the anaerobic fermentation unit and uses the same as an energy source of a self-generator or a combined heat and power generator, thereby advantageously realizing energy self-generation.

Advantageously, the dry anaerobic composting facility efficiently uses a ground space because it is laid under the ground, and solves problems including environmental pollution as well as complaints from inhabitants due to unpleasant facilities because it is mounted adjacent to residential areas.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:
1. A dry anaerobic composting facility comprising:
a dry anaerobic fermentation unit including
an anaerobic fermentation tank laid under the ground and composting organic waste pre-treated in absence of oxygen by methane fermentation,
covers doubly overlaid on an open top of the anaerobic fermentation tank,
a first rail mounted on a top side in a longitudinal direction of the anaerobic fermentation tank,
a second rail mounted on the first rail and moving in a width direction of the anaerobic fermentation tank along the first rail,
an agitator mounted on the second rail and agitating the organic waste contained in the anaerobic fermentation tank, and
a collector provided in an attic space of a ceiling of the cover and collecting biogas generated during the methane fermentation;
a pre-treatment unit laid under the ground and connected to the anaerobic fermentation tank, the pre-treatment unit including
a primary fermentation tank receiving the organic waste through a first gate, retaining the organic waste therein for predetermined period, and converting the organic waste into the low-molecular weight compounds through hydrolysis and acid fermentation,
the first gate disposed on a top of the primary fermentation tank, and
a substitution tank receiving the low-molecular weight compounds from the primary fermentation tank and the biogas from the collector and converting the low-molecular weight compounds from an aerobic state to an anaerobic state by substitution reaction and supplying anaerobic substances;
a post-treatment unit including
a post-aging tank laid under the ground with being connected to the anaerobic fermentation tank and aging and discharging the organic waste composted in the anaerobic fermentation tank, and
a second gate disposed on a top of the post-aging tank to discharge the compost;
a first barrier configured to rise and lower to isolate the pre-treatment unit from the dry anaerobic fermentation unit;
a fixed barrier configured to isolate the post-treatment unit from the dry anaerobic fermentation unit and provided with a transport screw,
wherein the agitator includes
a suction unit suctioning the organic waste in the anaerobic fermentation tank and grinding and agitating the organic waste,
a transport unit transporting the organic waste ground by the suction unit,
a discharge unit connected to the transport unit for discharging the organic waste,
a movement unit moving the suction unit in a vertical direction and moving the discharge unit in the longitudinal and width directions of the anaerobic fermentation tank, and
a control unit controlling the suction unit, the transport unit, the discharge unit and the movement unit.

2. The dry anaerobic composting facility according to claim 1, wherein the covers includes
a duct frame connected to an exterior vacuum pump to maintain an inside of the cover under vacuum, and
a plurality of solar modules provided on the surface of the cover for producing electricity from sunlight.

3. The dry anaerobic composting facility according to claim 2, further comprising:
a combined heat and power generator generating power using the biogas collected by the collector as an energy source and the electricity produced from the plurality of solar modules and supplying the power to a heater and a lighting provided in the anaerobic fermentation tank, the primary fermentation tank, the substitution tank and the post-aging tank, and to the first barrier and the transport screw.

4. The dry anaerobic composting facility according to claim 3, wherein the heater is a heat pipe or a warm water pipe.

5. The dry anaerobic composting facility according to claim 1, wherein the pre-treatment unit has a bottom surface inclined in one direction so that the organic waste is supplied to the anaerobic fermentation tank by self-weight.

6. The dry anaerobic composting facility according to claim 1, wherein the control unit further comprises
a sensor for acquiring data including at least one of viscosity of organic waste, temperature, pressure, ground particle size, water and gas discharge level and determining a state of the organic waste.

7. The dry anaerobic composting facility according to claim 1, wherein the movement unit comprises
a first motor for moving the agitator in the longitudinal direction of the anaerobic fermentation tank,
a second motor for moving the agitator in the width direction of the anaerobic fermentation tank, and
a hydraulic cylinder for moving the suction unit of the agitator in the vertical direction.

8. The dry anaerobic composting facility according to claim 1, wherein the suction unit comprises
a suction screw body rotating under control of the control unit,
suction screw blades mounted on the suction screw body, the suction screw blades moving the organic waste toward a center of the suction screw body upon rotation, and
a suction screw cover disposed on a rear surface of the suction screw body into which the organic waste is injected, the suction screw cover press-grinding the organic waste together with the suction screw blades.

9. The dry anaerobic composting facility according to claim 1, wherein the discharge unit comprises
a discharge screw body rotating under control of the control unit,
a discharge screw blade mounted on the discharge screw body, the discharge screw blade distributing the organic waste ground by the suction unit and transported along the transport unit, in a longitudinal direction of the discharge screw body upon rotation, and
a discharge screw cover disposed on the rear surface of the discharge screw blade.

10. The dry anaerobic composting facility according to claim 1, wherein the pre-treatment unit further includes a second barrier configured to rise and lower to isolate the primary fermentation tank and the substitution tank of from each other.

11. The dry anaerobic composting facility according to claim 1, further comprising
a downspout plate mounted on an end of the cover for collecting rain, and
a rain collection tank connected to the downspout plate for storing the rain collected by the downspout plate.

12. The dry anaerobic composting facility according to claim 2, wherein the duct frame is made of a flexible material so that the cover sags due to weight of the plurality of solar modules mounted on the surface of the cover and swells due to the biogas produced in the anaerobic fermentation tank.

13. The dry anaerobic composting facility according to claim 1, wherein the anaerobic fermentation tank has a bottom surface inclined in one direction, and includes
a leachate collection unit disposed in a lower part of the bottom surface for collecting a leachate of the organic waste, and
a filter disposed on a top of the leachate collection unit for allowing for injection of only leachate into the leachate collection unit.

\* \* \* \* \*